United States Patent [19]
Matsuo et al.

[11] Patent Number: 6,020,168
[45] Date of Patent: *Feb. 1, 2000

[54] PORCINE CNP GENE AND PRECURSOR PROTEIN

[75] Inventors: Hisayuki Matsuo, 5-15-141, 5-chome, Onoharahigashi, Minoo-shi, Osaka; Kenji Kangawa, Miyazaki-ken; Naoto Minamino, Osaka; Shoji Tanaka, Hyogo-ken; Kayoko Fuchimura, Osaka; Yasunori Tawaragi, Saitama-ken, all of Japan

[73] Assignees: Suntory Limited; Hisayuki Matsuo, both of Osaka, Japan

[*] Notice: This patent is subject to a terminal disclaimer.

[21] Appl. No.: 07/728,220

[22] Filed: Jul. 12, 1991

[30] Foreign Application Priority Data

Jul. 13, 1990 [JP] Japan .................... 2-186583

[51] Int. Cl.[7] .................. C12P 21/06; C07H 17/00; C07K 14/00
[52] U.S. Cl. .................. 435/69.4; 536/23.53; 530/300; 530/350
[58] Field of Search ............... 536/27; 530/350, 530/326, 324, 300

[56] References Cited

PUBLICATIONS

Sudoh et al, "Biochemical and Biophysical Research Communications", Academic Press, Inc., Apr. 30, 1990, pp. 863–870.

Maekawa et al, "Biochemical and Biophysical Research Communications", Academic Press, Inc., Nov. 30, 1988, pp. 410–416.

Tawaragi et al, "Biochemical and Biophysical Research Communications", Academic Press, Inc., Oct. 30, 1990, pp. 627–632.

Minamino et al, "Biochemical and Biophysical Research Communications" Academic Press, Inc., Jul. 31, 1990, pp. 973–979.

Maekawa et al. 1988 Biochem Biophys Res Commun, 157 (1) : 410–416.

Kita et al. 1989 Life Science 44: 1541–1545.

Steinhelper et al 1990 Hypertension 16(3): 301–307. Abstract.

*Primary Examiner*—Karen Cochrane Carlson
*Attorney, Agent, or Firm*—Pillsbury Madison & Sutro LLP

[57] ABSTRACT

The gene and cDNA of a procine derived CNP (C-type natriuretic peptide), and a procine derived CNP precursor protein and derivatives thereof are disclosed. The proceine derivative CNP precursor is represented by the following amino acid sequence:

```
Met His Leu Ser Gln Leu Leu Ala Cys Ala
Leu Leu Leu Thr Leu Leu Ser Leu Arg Pro
Ser Glu Ala Lys Pro Gly Ala Pro Pro Lys
Val Pro Arg Thr Pro Pro Gly Glu Glu Val
Ala Glu Pro Gln Ala Ala Gly Gly Gly Gln
Lys Lys Gly Asp Lys Thr Pro Gly Gly Gly
Gly Ala Asn Leu Lys Gly Asp Arg Ser Arg
Leu Leu Arg Asp Leu Arg Val Asp Thr Lys
Ser Arg Ala Ala Trp Ala Arg Leu Leu His
Glu His Pro Asn Ala Arg Lys Tyr Lys Gly
Gly Asn Lys Lys Gly Leu Ser Lys Gly Cys
Phe Gly Leu Lys Leu Asp Arg Ile Gly Ser
Met Ser Gly Leu Gly Cys.
```

These derivatives are novel and have natriuretic and hypotensive activities.

15 Claims, 8 Drawing Sheets

Fig. 1

AspLeuArgValAspThrLysSerArgAlaAlaTrpAlaArgLeuLeuHisGlu
5'                                              3'    A   C
GACCTGCaGGTGGACACCAAGTCCCGGGCTGCCTGGGC          GT CT
                                                  G  T
      KF225                                       KF206

HisProAsnAlaArgLysTyrLysGlyGlyAsnLysLysGlyLeuSerLysGly
    A
GT   GGNTT                                      5'
    G

CysPheGlyLeuLysLeuAspArgIleGlySerMrtSerGlyLeuGlyCys
                    3'                                 5'
TTCGACCTGGCCTAACCGAGGTACAGACCGGACgtCACG
                         KF226

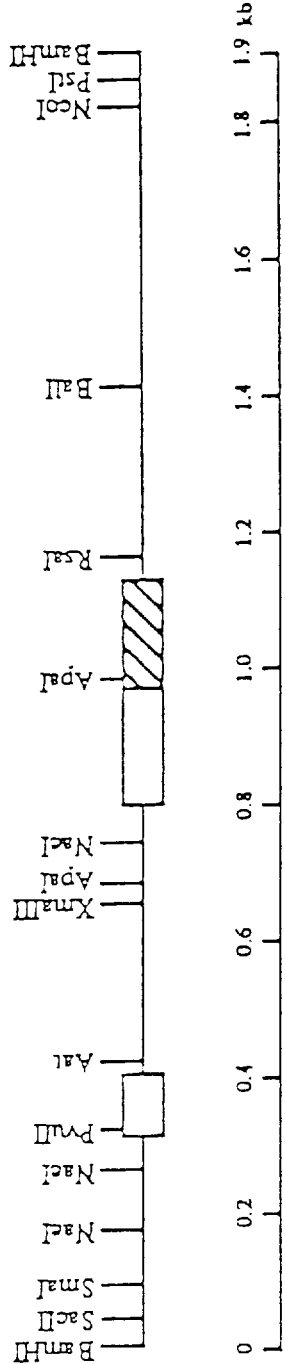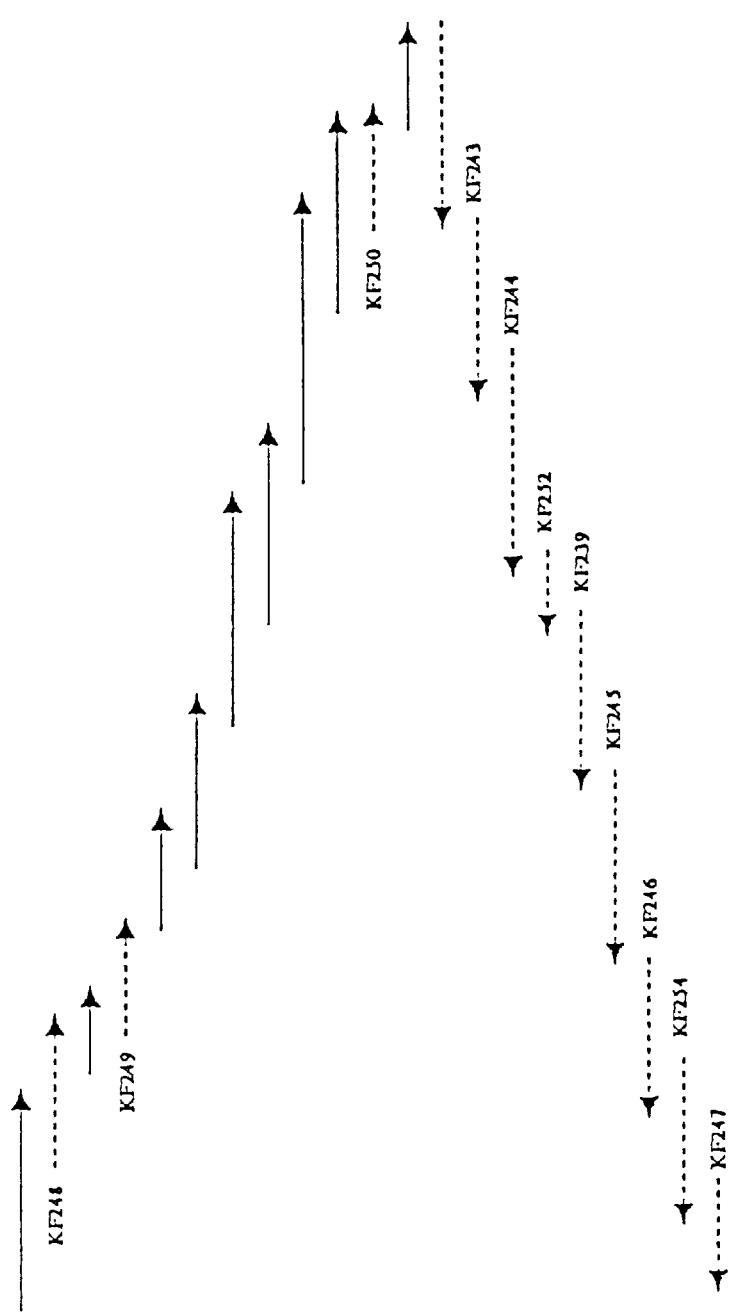
Fig. 2(a)
Fig. 2(b)

Fig. 2(c)

| | 5' | 3' |
|---|---|---|
| KF239 | CTTGGACAAACCCTTCTTGTTG | |
| KF243 | GGGGCTGGCAGATAAAC | |
| KF244 | AGCCGCTTCTGACCTTG | |
| KF245 | GTGAAGGGACGCACGAC | |
| KF246 | TACCGGCGCACATCTGG | |
| KF247 | GTCCAGTGCTGCGCGG | |
| KF248 | CCGCGCAGCACTGGGAC | |
| KF249 | CCCAGATGTGCCGGT | |
| KF250 | CAAGGTCAGAAGCGGCT | |
| KF252 | AGACCGGCTTGCGGCAC | |
| KF254 | GCTTCGGAGGGCCGGAG | |

| Fig. 3 |
|---|
| Fig. 3(a) |
| Fig. 3(b) |

Fig. 3(a)

```
                                                                              80
GGATCCCCTCCGGGGTGGGAAGAGAGGGTGGGGCAGAGGGGAGCCCCCGCGGCCCCTCCCGGCCTTCGGCGCGTGCA
                                                                             160
TTGGCCGGGGCGGCCCTTGTGGGCGGGAGGATGACATCAGCGGCAGTTGGATTATAAAGCGCGAGCGGAGCCACGGGCT
Y box   GC box          GC box                            TATA box
                                                                             240
CAGAGCGCACCCAGCCGCGCGCCGCGCCAGCACTGGGGACTCGCGGCACCGAGCCCGGCCAGTCTGTCCGCGCTCGCT
                                                                             320
TGCCAGTCTGCCCGGCCCCGTGCACCTCTCTGCGCGGCCCCGATCTGCGCCCTCCACCCCACAGGCACCATGCACCTCTC
                                                                             400
                                                                 MetHisLeuSe
CCAGCTGCTGGCCTGCGCTCTGCTGCTGCTCACGCTCCTCTGCGCCCTCCGAAGCCCAAGCCCGAGCGCCGAAGG
rGlnLeuLeuAlaCysAlaLeuLeuLeuLeuThrLeuLeuSerGluAlaAlaLysProProLys
                                                                             480
TGGGTGCTGTCGCAGGACGTCGAACTGTGAGGGGGTCTAGGAGGTGCGCGGTGAGAGCTGGGCGCCTTCGAAGCTGGGGAG
                                                                             560
                     ProSerGluAlaAlaLysProProLys
AGCAGCAGAGGGGCCAGGAAGGCGGCTCTCTCCCCAGATGTGCGCCGGTAAGAGCTGGGCGCCTTCGAAGCTGGGGAG
                                                                             640
AACGTCTCGCAAAACGCGCAGCCGCGCGGCGCGTGGTCAGCCCGGCCGGAGAGAGGGCGAGGGACTCCCT
                                                                             720
GAGGAAGGGACAGCGGCGGCCGGGCGTGTGCGGGCGTGGCAGGTGATGCAGGGCCCAACTATCCTGCACCTGTGGGGAGGC
                                                                             800
TTGAAAGGGACAAACCGCGCCGGGCGCGTGCGCCCTGGAGCATCAGCGGCCCCACAAAGTCCCCCGCCCCTGCCGTCGT
                                                                             880
GCGTCCCTTCACTTACCTGTTCTTTCCCCTCGACAGGTCCCTCGAACTCCGCAGGGAGGAGGTGGCCGAGCCCCAG
                                                            ValProArgThrProProGlyGluAlaAlaGluProGln
```

Fig. 3(b)

```
GCTGCGGGCGGCGGTCAGAAGAAGGGCGACAAGACTCCTGGGGCGGTGGCCGCCAACCTCAAGGGCGACCGGTCTGACT     960
AlaAlaGlyGlyGlyGlnLysLysGlyAspLysThrProGlyGlyGlyGlyAlaAsnLeuLysGlyAspArgSerArgLe
GCTCCGGGACCTGCGCGTGACACCAAGTCTCGGGGCGTGGCCCGCCTTCTGCACGAGCACCCAACGCGCCAAAT        1040
uLeuArgAspLeuArgValAspThrLysSerArgAlaAlaTrpAlaArgLeuLeuHisGluHisProAsnAlaArgLysT
ACAAAGGAGGCAACAAGAAGGGTTTGTCCAAGGCTGCTTCGGCCTCAAACTGACCGGATCGGCTCCATGAGCGGCCTG    1120
yrLysGlyGlyAsnLysLysGlyLeuSerLysGlyLeuCysPheGlyLeuLysLeuAspArgIleGlySerMetSerGlyLeu 1200
GGATGTTAGTGCGGCGACCCCTGGCGGCGGTGAGTACCACCCAACCCTGGCCTCCGGGCGCTCTTGGCACACCCAGCTCC
GlyCys***                                                                          1280
CCCGAGAAGGCCCCCAGAACCAGCCTGAACCCGTGCCGCCGGTCTCCCCTCTGATCCCCAGACTTTGGGACCATT       1360
CCGCCTCCCAGCCGACCTTTGGAGGGGAGCCAACCGACTCCAGCACAAGACTGAGGGCGTGTGCCAGACATTTGTCCCAA  1440
GACCGTTTATCATTCCATTTCACAGATGGGGGAAATTGAGGGATAAAGTGGCCAGGTAATTTTGGCAAGGTCAGAAGCGG  1520
CTCAGCATGGATGAACGCACCTGGCTGCCTCTGGGGAAACAGGCCAGCTTGGTGGAGTCCTGCCCATCCCAGGAACATAAG 1600
GCAGCCAGCAGCACTGGCCCCAGTTTGCCAGTTGGGGGTCTTGAAGAGTGATCCTGGCTGATGGGAGCAGAGGAGAA    1680
GGGCAGACCCCACAGGTCAAGGGTAAGTTTATCTGCCGAAATGGGACCGACGCGGATCAAGATCCGTGCCCTCACGGTCA  1760
GGACAGCTCCCTGGGTCTGTTGTCCCTGAAATGGGACCGACGCGGATCAAGATCCGTGCCCTCACGGTCGAGAGAATAGC  1760
CCTCTGTTGGCATCACGGAGGTGCATTCGCCCCAGAACATTCGGCTCTCTTGTCCCTTCTCTAAACCATGGCTGTGTGGCA 1840
AACTGGTCTGTCCAGGTCCTGACGCCTCTGCAGCCTGTGCGACTTCAGGATCC
```

Fig. 5

```
-143 GCACCCAGCCGGCCG                                                                              -127
-126 CGCAGCACTGGGACTCGGCCCGGCCACGCAGCCCGGCCAGTCTGCTCCGCTCGGCTTGCCAG                                -64
 -63 TCTGCCGCCGGCCCCGGCCCGTGCACCTCTCTGCGCCGATCTGCGCCCCTCCACCCACAGGCACC                              -1
   1 Met His Leu Ser Gln Leu Leu Ala Cys Ala Leu Leu Thr Leu Leu                                   48
     ATG CAC CTC TCC CAG CTC CTG GCT TGC GCC CTG CTG ACG CTC CTC
       1                                                      16
  49 Ser Leu Arg Pro Ser Glu Ala Lys Pro Gly Ala Pro Lys Val Pro                                   96
     TCG CTC CGG CCC TCC GAA GCC AAG CCC GGA CCC AAG GTC CCT
      17                                                      32
  97 Arg Thr Pro Pro Gly Glu Val Ala Glu Pro Gln Ala Ala Gly Gly                                  144
     CGA ACT CCG CCA GGG GAG GTG GCC GAG CCC CAG GCT GCG GGC
      33                                                      48
 145 Gly Gln Lys Lys Lys Gly Asp Lys Thr Pro Gly Gly Gly Ala Asn Leu                              192
     GGT CAG AAG AAA AAG GGC GAC AAG ACT CCT GGG GGT GGC GCC AAC CTC
      49                                                      64                              80
 193 Lys Gly Asp Arg Ser Arg Leu Leu Arg Asp Leu Arg Val Asp Thr Lys                              240
     AAG GGC GAC CGG TCT CGA CTC CTC CGG GAC CTG CGC GTG GAC ACC AAG
      65                                                      80                              96
 241 Ser Arg Ala Ala Trp Ala Leu Leu His Glu Pro Asn Ala Arg                                      288
     TCT CGG GCG GCG TGG GCC CTT CTG CAC GAG CCC AAC GCG CGC
      81                                                     112
 289 Lys Tyr Lys Gly Gly Asn Lys Lys Gly Leu Ser Lys Gly Cys Phe Gly                              336
     AAA TAC AAA GGA AAC AAG AAG GGT TTG TCC AAG GGC TGC TTC GGC
     113                                                     126
 337 Leu Lys Leu Asp Arg Ile Gly Ser Met Ser Gly Leu Gly Cys *                                    384
     CTC AAA CTG GAC CGG ATC GGC TCC ATG AGC GGC CTG GGA TGT TAG TGC
 385 GGCGACCCCTGGCGGCGGGTGAG 407
```

PORCINE CNP GENE AND PRECURSOR PROTEIN

BACKGROUND OF THE INVENTION

This invention relates to the gene and CDNA of a as porcine derived CNP (C-type natriuretic peptide), as well a porcine derived CNP precursor protein.

Peptides assignable to two different peptide families that are named "atrial natriuretic peptide (ANP)" and "brain natriuretic peptide (BNP)" have recently been discovered as hormones or nerve transmitters that regulate the homeostatic balance of body fluid volume and blood pressure in vivo. The structures of those peptides, the mechanism of their biosynthesis, as well as their physiological actions have also been unravelled.

Very recently, the present inventors discovered from porcine brain a novel peptide that was named "C-type natriuretic peptide (CNP)" and that belonged to a third family of peptides.

The first clue to the discovery of ANP was reported by de Bold et al. in 1981. Finding that significant diuresis occurred when a rat's atrial crude extract was injected intravenously into another rat, de Bold et al. reported the existence of a natriuresis promoting factor in the atrium (de Bold, A. J. et al., Life Sci., 28, 89, 1981). Kangawa et al. later isolated that factor from human atrium, unravelled its structure and named it "atrial natriuretic peptide (ANP)" (Kangawa, K. et al., Biochem. Biophys. Res. Commun., 118, 131, 1984; Kangawa, K. et al., Nature, 313, 397, 1985; Japanese Patent Publication No. 19520/1988; Japanese Patent Public Disclosure No. 184098/1985 and 260596/1985). It has been found that human ANP (hANP) as it occurs in the atrium is classified into three types, α-, β- and γ-types, according to the molecular weight; α-type hANP (α-hANP) is a single-stranded peptide that consists of 28 amino acids having a single S—S bond in the molecule; β-type hANP (β-hANP) is an antiparallel dimer having an S—S bond formed between the molecules of α-hANP; and γ-type hANP (γ-hANP) is a high-molecular weight protein composed of 126 amino acids, with x-hANP being contained in the C-terminal portion. Further, CDNA for hANP has been isolated and the routes of biosynthesis of α-, β- and γ-hANP have been identified the basis of analysis of that CDNA, leading to the conclusion that each of those three types of hANP is biosynthesized from a common precursor protein (Oikawa, S. et al., Nature, 309, 724, 1984).

It is already known that among the three types of hANP, α-hANP is chiefly secreted into blood.

Ever since the structure of hANP was first unravelled, the structures of ANPs derived from other mammals have also been studied (Japanese Patent Public Disclosure Nos. 184097/1985 and 7298/1986) and today the following knowledge is available: ANPs have similar amino acid sequences over a broad spectrum of mammals ranging from rodents to humans; α-type ANP (α-ANP) has the same amino acid sequence in higher mammals including humans, dogs and pigs; and α-type ANPs derived from rats and rabbits have entirely the same amino acid sequence as α-hANP except that the methionine residue in position 12 is replaced by an isoleucine residue (Oikawa, S. et al., Biochem. Biophys. Res. Commun., 132, 892, 1985; Forssmann, W. G. et al., Anat. Embryol., 168, 307, 1983).

The first ANP isolate was obtained from the atrium but later studies involving the preparation of anti-ANP antibodies and examination of their distribution in vivo have shown that ANP also occurs in the brain as well as in the atrium, except that in the brain the N-terminus of α-ANP is cut off to yield shorter α-ANP [4–28] and α-ANP [5–28] (Ueda, S. et al., Biochem. Biophys. Res. Commun., 149, 1055, 1987). Since ANP-containing neurons have been reported to occur in the hypothalamus and pontine tegmentum of the brain (Cantin, M. et al., Histochemistry, 80, 113, 1984; Saper, C. B. et al., Science, 227, 1047, 1985), it is speculated today that ANP may also work in the brain as a nerve transmitter that participates in the regulation of the cardiovascular system. The physiological actions of ANP are diverse and are not limited to a marked natriuretic action alone; it has recently been found that it is capable of not only lowering the blood pressure but also suppressing the production of aldosterone from the adrenal cortex. It is therefore clear today that ANP as it is secreted from the atrium into blood not only works as a hormone that regulates the homeostatic balance of body fluid volume and blood pressure but that in the brain it also works as a nerve transmitter for the nerve system to regulate the homeostatic balance of body fluid volume and blood pressure.

Brain natriuretic peptide (BNP) was first isolated from porcine brain and identified by Sudoh et al., in 1988 (Sudoh, T. et al., Nature, 332, 78, 1988). The first BNP isolate (pBNP-26) is a peptide that consists of 26 amino acid residues having a single S—S bond in the molecule and although it is similar to ANP in structure, i.e., in terms of primary amino acid sequence and the mode of S—S binding (producing a ring structure composed of 17 amino acid residues), BNP is clearly distinguishable from ANP. As in the case of ANP, natriuretic and hypotensive actions have been verified for BNP, which has therefore been named "brain natriuretic peptide (BNP)". At a later time, pBNP-32 composed of 32 amino acid residues having 6 amino acids attached to the N-terminus-of pBNP-26 was isolated from porcine brain (Sudoh, T. et al., Biochem. Biophys. Res. Commun., 155, 726, 1988); from porcine atrium, a peptide named "γY-BNP" which was composed of 106 amino acids was also isolated and identified (Minamino, N. et al., Biochem. Biophys. Res. Commun., 157, 402, 1988).

As of today, the cDNAs of human and rat BNPs have been isolated and the structures of precursors for those BNPs have also become clear (Sudoh, T. et al., Biochem. Biophys. Res. Commun., 159, 1427, 1989; Kojima, M. et al., Biochem. Biophys. Res. Commun., 159, 1420, 1989).

On the basis of these results, it has been found that the peptides of the BNP family are biosynthesized from precursors that are entirely different from ANP.

As already mentioned, BNP was first isolated from the brain. It was later found that BNP was present in porcine brain in an amount ten times as much as ANP and that like ANP, BNP also occurred in the atrium (though in an amount of only 2–3% of ANP) to be secreted into blood (Minamino, N. et al., Biochem. Biophys. Res. Commun., 155, 740, 1988; Aburaya, M. et al., Biochem. Biophys. Res. Commun., 165, 872, 1989). From these facts, it was found that like ANP, BNP worked as a nerve transmitter in the brain and also worked as a hormone to be secreted from the atrium into blood, in either case helping regulate the homeostatic balance of body fluid volume and blood pressure. As exemplified by natriuretic peptides, not a single peptide but a plurality of peptides can participate in the regulation of a certain physiological action in vivo (e.g. homeostasis of body fluid volume and blood pressure) and opioid peptide, tachykinin and endothelin have so far been recognized as other examples of such peptides. It has been known that three different families exist for each of those peptides (Hollt, V., Trend Neuro Sci., 6, 24, 1983; Nakanishi, S., Physiol. Review, 67, 1117, 1987; Inoue, A. et al., Proc. Natl. Acad. Sci., U.S.A., 86, 2863, 1989). This had increased the possibility that aside from the natriuretic peptides so far been known to be assignable to ANP and BNP families, peptides that could be classified into a third family might exist. In this regard, the present inventors very recently succeeded in discovering two novel peptides from porcine brain that did not belong to either ANP or BNP family but that belonged to a third family of natriuretic peptides. Those peptides were named "C-type natriuretic peptide (CNP)". The first discovered CNP was a peptide composed of 22 amino acid residues (this peptide is hereinafter abbreviated as "CNP-22"); the structure of this peptide is similar to but clearly distinguishable from those of ANP and BNP. Stated more specifically, CNP-22 is similar to ANP and BNP in that it has a ring structure composed of 17 amino acid residues based on intramolecular S—S binding and that the primary amino acid sequence forming this ring structure in CNP-22 is highly homologous to that in α-ANP and BNP-32. As a matter of fact, 12 out of the 17 amino acid residues was identical among those three peptides. However, except for the ring structural portion, CNP-22 is entirely different from α-ANP and BNP-32 in N- and C-terminal portions. A particularly characteristic feature is found in the structure of the C-terminal portion; in the case of α-ANP, 5 amino acid residues (in the case of BNP-32, 6 amino acid residues) are present at the C-terminus of the cysteine residue forming the ring structure, thereby producing a "tail" structure, but no such "tail" structure is present in CNP-22 since its C-terminus is a cysteine residue.

As described above, CNP-22 has an obviously different structure than α-ANP and BNP-32; in addition, it has been verified that when administered to rats, CNP-22 exhibits obvious natriuretic and hypotensive actions it has therefore been found that CNP-22 is a new peptide assignable to a third family of natriuretic peptides in vivo (Japanese Patent Application No. 105047/1990). The present inventors later prepared anti-CNP-22 antibodies and purified from porcine brain those peptides which exhibited immunoreactivity with those antibodies. As a result, the present inventors successfully isolated a peptide named "CNP-53". An analysis of its structure showed that CNP-53 was a peptide composed of 53 amino acid residues containing CNP-22 in the C-terminus, namely, a peptide having 31 additional amino acid residues attached to the N-terminus of CNP-22 (see the commonly assigned patent application filed on the same date as the subject application).

In short, the following observations have been obtained to date: at least three families (ANP family, BNP family and CNP family) of natriuretic peptides having obviously different structures occur in mammals; peptides of the ANP and BNP families are not only secreted from the atrium into blood and work as hormones that regulate the homeostatic balance of body fluid volume and blood pressure; they are also biosynthesized in the brain, where they work as nerve transmitters for the nerve system to regulate the homeostatic balance of body fluid volume and blood pressure. However, the recently discovered peptides of the CNP family (CNP-22 and CNP-53) occur in so smaller amounts in the brain than ANP and BNP that as of today no detailed information has been obtained with respect to the mechanism of CNP biosynthesis, their distribution in vivo and physiological actions.

SUMMARY OF THE INVENTION

The present invention has been accomplished under these circumstances and has as an object isolating and analyzing the genes and cDNAs of porcine CNPs (CNP-22 and CNP-53) and their precursors so as to identify the primary amino acid sequence of the precursor protein of porcine CNP, as well as to provide a process for producing by genetic engineering all or part of the protein encoded by the gene of said precursor protein.

BRIEF DESCRIPTION OF THE DRAWINGS

FIG. 1 is a diagram in which the base sequences of the synthetic DNA primers (KF 225 (see SEQ. ID. NO. 17) and KF 226 (see SEQ. ID. NO. 19) used to specifically amplify the CNP-53 encoding gene region from a porcine chromosomal gene using PCR and the DNA mixed probe (KF 206) (see SEQ. ID. NO. 18) used to isolate the gene are shown together with the primary amino acid sequence of CNP-53 ( see SEQ. ID. NO. 22);

FIG. 2(a) is a restriction enzyme map for the chromosomal gene (BamHI DNA fragment) of a porcine CNP precursor protein;

FIG. 2(b) is a diagram showing the strategy of determining the DNA base sequence of the gene;

FIG. 2(c) is a diagram showing the base sequence of the synthetic DNA primer used in base sequence determination (see SEQ. ID. NOS. 3, 4, 5, 6, 7, 8, 9, 10, 11, 12, 13);

FIG. 3 is a diagram showing the DNA base sequence (see SEQ. ID. NO. 1) of the chromosomal gene (BamHI DNA fragment) coding for the porcine CNP precursor protein and the primary amino acid sequence (see SEQ. ID. NO. 20) of the porcine CNP precursor protein encoded by the exons in the structural gene region;

FIG. 5 is a diagram showing the whole base sequence (see SEQ. ID. NO. 2) of CNP cDNA and the primary amino acid sequence (see SEQ. ID. NO. 20) of the porcine CNP precursor protein encoded by the cDNA.

DETAILED DESCRIPTION OF THE INVENTION

Figure 4:
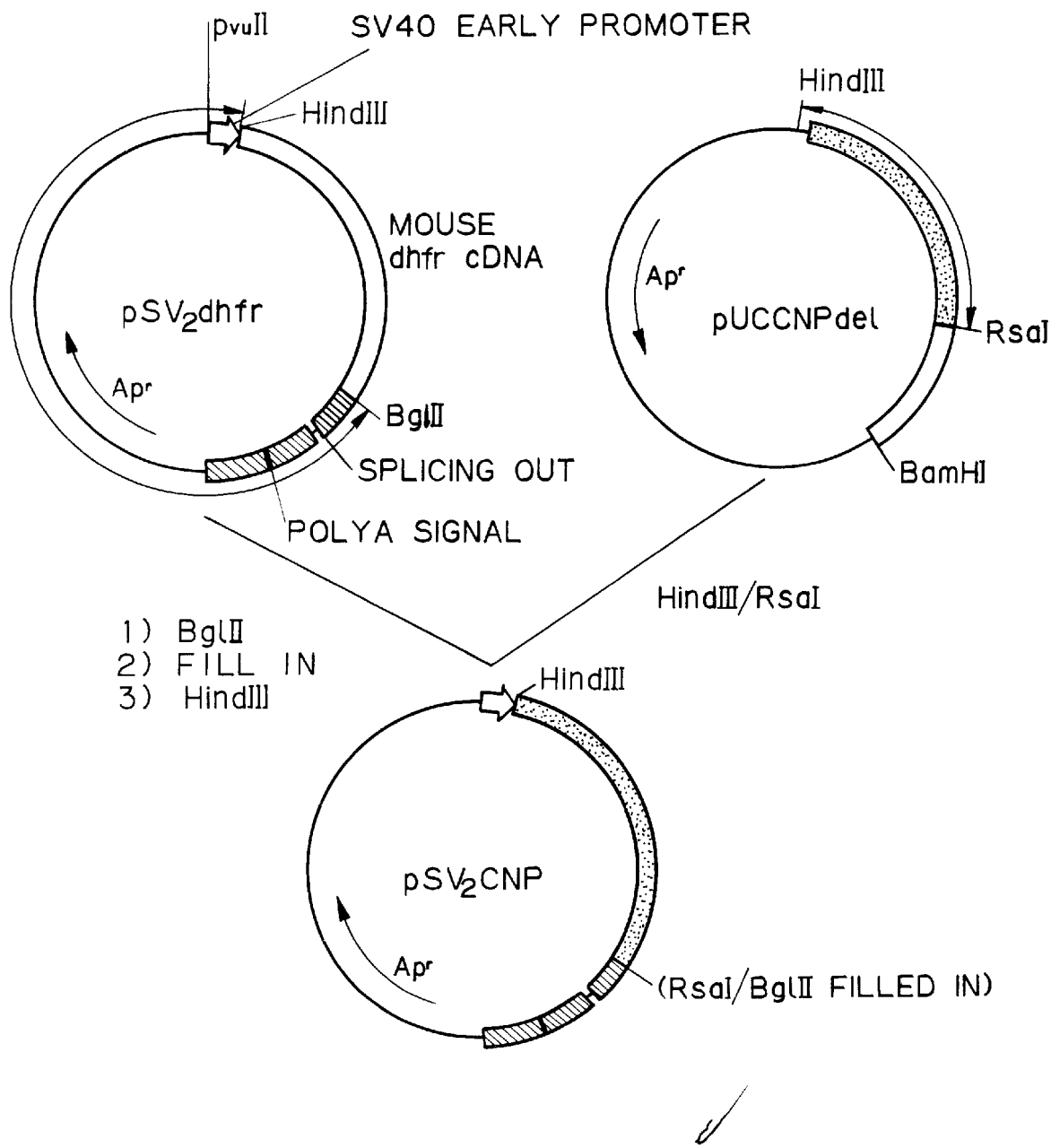
FIG. 4 illustrates how to prepare animal cell expression vector pSV2CNP.

The CNP-22 and CNP-53 previously isolated by the present inventors occurred in porcine brain in extremely smaller amounts than ANP and BNP. In addition, the tissue responsible for the production of those peptides in the brain is yet to be identified. Under the circumstances, the present inventors thought that it would be difficult to isolate directly the cDNA corresponding to CNP and identify the structure of the CNP precursor protein on the basis of analysis of that cDNA. Instead, the present inventors planned a project for isolating CNP gene from porcine chromosome and identifying the structure of porcine CNP precursor protein by analyzing the isolated chromosome.

In the present invention, a DNA probe to be used for isolating CNP gene was prepared by the following procedure. First, as shown in FIG. 1, DNA primers (KF 225 and KF 226) corresponding to the primary amino sequence of CNP-53 in the N- and C-terminal portions were prepared. In FIG. 1, N appearing in the base sequence of KF 206 denotes either one of A, T, C or G. Then, using those primers, polymerase chain reaction (PCR) was performed in accordance with the method of Saiki et al. (Saiki, R. K. et al., Science, 239, 487, 1988), whereby only the DNA region of the porcine chromosoma gene that coded for the primary amino acid sequence of CNP-53 was amplified specifically. The amplified DNA was introduced into a plasmid vector before a clone (DH1/pCNP5) incorporating the desired DNA was isolated.

Plasmid pCNP5 was recovered from the thus obtained DH1/pCNP5 and analyzed to verify that it contained a DNA fragment composed of 147 base pairs (bp) amplified by PCR (which DNA fragment is hereunder abbreviated as DC-53) and that DC-53 was a DNA coding for the primary amino acid sequence of CNP-53. From these results, it was at least clear that no introns were contained in the gene region coding for the primary amino acid sequence of CNP-53. Subsequently, the thus prepared DNA probe (DC-53) was used to screen a porcine chromosomal gene library (λ-phage incorporating the porcine chromosomal gene fragment), whereby a clone (λCNP6) hybridizing with DC-53 was obtained. Upon analysis, the clone λ-CNP6 was found to contain ca. 14 kbp of the porcine chromosomal gene. It was also found that a BamHI DNA fragment composed of ca. 2 kbp of that 14 kbp would hybridize with a DC-53 DNA probe. On the basis of these results, the whole base sequence of the BamHI DNA fragment composed of ca. 2 kbp was determined by the procedure shown in FIG. 2. As a result, it was found that the BamHI DNA fragment contained not only a structural gene region coding for the whole amino acid sequence of the porcine CNP precursor protein but also the promoter region of porcine CNP gene (see FIG. 3).

First, as regards the promoter region, a TATA box which was shared by the promoter regions of eukaryotic genes was found to exist in positions 133–138 of the DNA base sequence shown in FIG. 3; it was also found that two GC boxes and one Y box which were believed to participate in the control of gene expression were present upstream of the TATA box. From these facts, it was concluded that the region under consideration was the promoter region of the CNP precursor gene.

As regards the structural gene region, ATG was present in positions 310–312 downstream (3' side) the base sequence of the TATA box; since the ATG was the first methionine codon that appeared downstream (3' side) of the TATA box and since the base sequence around that codon was in agreement with the consensus sequence of a translation initiation codon, A/G NNATG (N denotes either one of A, T, G and C), which is known to exist in eukaryotes. Based on these facts, the present inventors estimated that the ATG of interest would be a translation initiation codon for the porcine CNP precursor.

Downstream of this translation initiation codon ATG, an open reading frame coding for 40 amino acid residues exists and continues up to a translation termination codon (TGA) present in positions 430–432. However, amino acid sequences that correspond to CNP-22 and CNP-53 do not appear in the primary amino acid sequence of peptide that is predicable from said open reading frame. On the other hand, the BamHI DNA fragment of interest contains an open reading frame that codes for 134 amino acid residues from positions 725 to 1126 of the base sequence and it was found that primary amino acid sequences that corresponded to CNP-22 and CNP-53 appeared in the primary amino acid sequence of peptide that was predictable from said open reading frame. On the basis of these analyses, it was found that the structural gene of porcine CNP contained at least one intron; in other words, the porcine CNP precursor protein on the gene is encoded in at least two exons. This is also supported by the following two facts; a base sequence similar to C/A AGGT A/G ATG which is known to be the consensus sequence of a splicing donor exists in an area near position 400 of the base sequence; and a base sequence similar to (Py)n N C/T AGG (Py denotes a pyridine residue, and N denotes either one of the bases A, T, C and G) which is known to be the consensus sequence of a splicing acceptor exists on the 5' side of position 840 of the base sequence. On the basis of these facts, the present inventor assumed that the DNA region from position 399 to position 838 of the base sequence might be an intron, which could probably be eliminated by splicing when a mature mRNA coding for the CNP precursor protein was produced. In other words, it was estimated that the CNP precursor protein would be a polypeptide composed of a total of 126 amino acid residues that was encoded by two exons, the first one starting at position 310 of the base sequence and ending at position 399 and the second one starting at position 838. In order to verify this estimation, the present inventors expressed the structural gene region of the CNP precursor gene in animal cells and analyzed the structure of mRNA transcribed from that structural gene, as well as the protein translated from said mRNA.

To this end, the present inventors first prepared a plasmid pSV2CNP having the structural gene region of the CNP precursor gene linked to the initial promoter of SV 40 (see FIG. 4) and introduced the plasmid into COS-1 cells (which cells are hereinafter abbreviated as COS-1/pSV2CNP), whereby the structural gene was expressed in the animal cells under the control of the SV 40 promoter.

For mRNA analysis, the following procedure was taken. The whole RNA was extracted from COS-1/pSV2CNP and, subsequently, using an oligo-dT cellulose column, poly(A)$^+$ RNA was prepared, which was used to prepare a cDNA library. Then, the cDNA library was screened using DC-53 DNA to isolate a clone DH1/pCNP cDNA 1 that would hydridize with the DNA probe. A plasmid pCNP cDNA 1 was further isolated from the clone to determine the total base sequence of the cDNA region. As a result, it was found that the mature MRNA (cDNA) that derived from the structural gene of CNP gene did not contain the region which the present inventors predicted would correspond to an intron (see FIG. 5). The DNA region located in positions 400–838 of the base sequence shown in FIG. 3 was an intron but it was found to be eliminated by splicing when a mature mRNA coding for the CNP precursor protein was prepared. Under the circumstances, the present inventors finally succeeded in establishing the positions of exons and an intron in the structural gene region of the CNP gene. They also succeeded in identifying the CNP precursor protein as a polypeptide composed of 126 amino acid residues having the primary amino acid sequence shown in FIG. 5. In the thus identified primary amino acid sequence of the porcine CNP precursor protein (which is hereunder abbreviated as prepro CNP), CNP-22 and CNP-53 were present in the C-terminal region of PrePro CNP whereas a region rich in hydrophobic amino acid residues (in positions 10–16 of the primary amino acid sequence shown in FIG. 5) was present in the N-terminal region of PrePro CNP and, in view of these facts, there is a high possibility that the signal peptide necessary for secretion will exist in the N-terminal region of PrePro CNP.

With the above-discussed facts taken into consideration, CNP-22 and CNP-53 are presumably biosynthesized by the following pathway. First, PrePro CNP composed of 126 amino acid residues is translated from mRNA. Then, the signal peptide present in the N-terminal region of the PrePro CNP is cleaved for conversion to Pro CNP in the process of secretion. Further the Pro CNP is cleaved by a processing enzyme at specific positions (between positions 73 and 74 of the primary amino acid sequence and between positions 104 and 105 of the same sequence that is shown in FIG. 5) to be converted to CNP-53 and CNP-22.

In order to verify this presumption, the present inventors then analyzed the protein in the culture supernatant of COS-1/pSV2CNP by the following procedure. First, the liquid supernatant of a culture of COS-1/pSV2CNP was collected and concentrated. Then, the proteins and peptides contained in the concentrate were fractionated by molecular weight using Sephadex G-75. A portion of each elution fraction was then subjected to radioimmunoassay (RIA) using an anti-CNP-22 antiserum, whereby the amounts of peptides and proteins that were present in each fraction and that showed immunoreactivity with the anti-CNP-22 antibody were determined.

Figure 6:
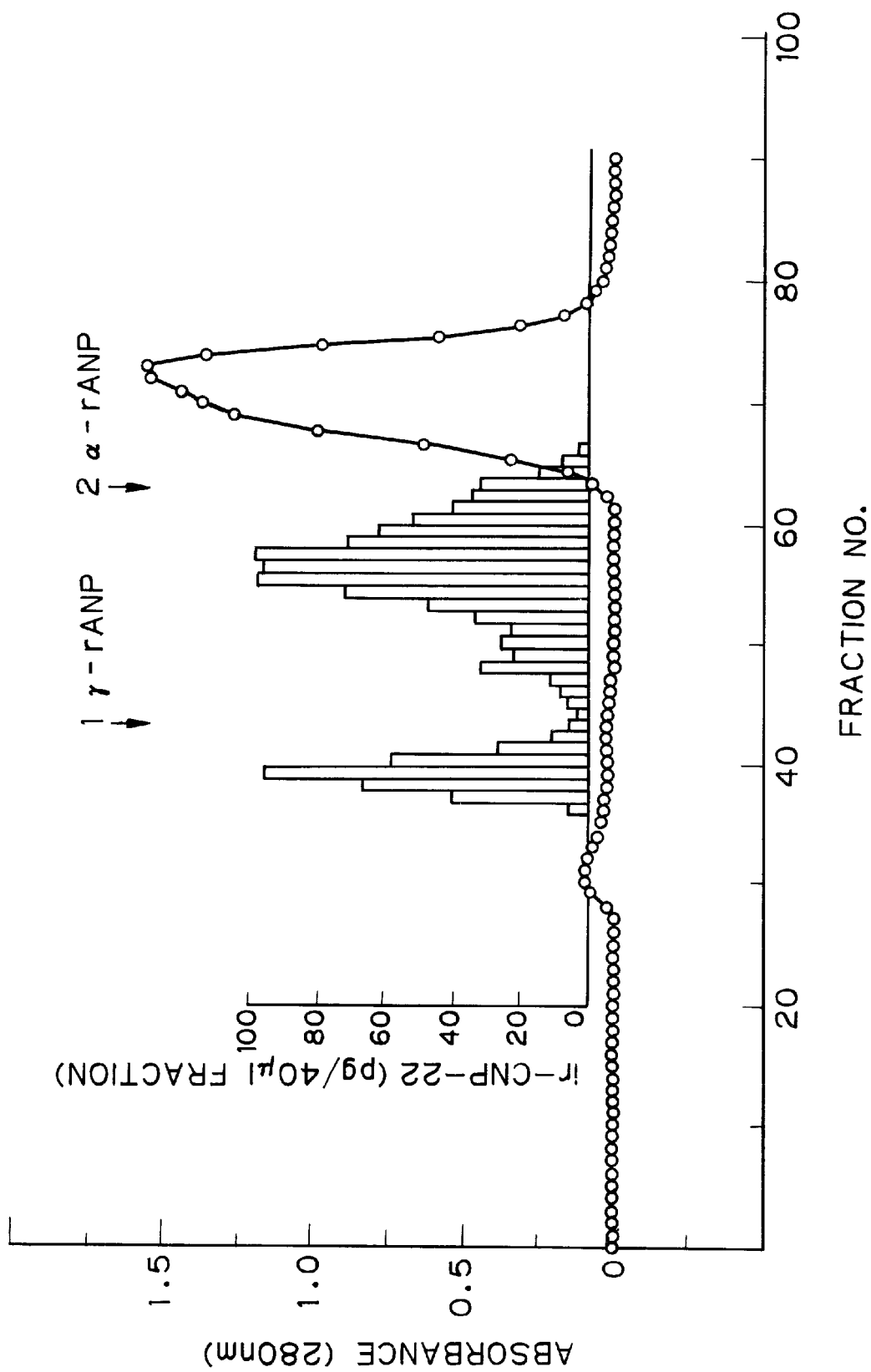
FIG. 6 is a chart showing the elution profile obtained by separating on a sephadex G-75 gel filtration column the proteins and peptides contained in the culture supernatant of COS-1/pSV2CNP 1 cells, as well as the immunoreactivity of the resulting elution fractions with an anti-CNP-22 antiserum.

The results are shown in FIG. 6, in which the positions of elution of γ-rANP (1) and α-rANP (2) from the column are indicated by an arrow. As one can see from FIG. 6, proteins and peptides that showed immunoreactivity with the anti-CNP-22 antiserum were present in fractions with molecular weights of ca. 16 kd and in fractions with molecular weights of ca. 3–10 kd. This led to the conclusion that Pro CNP was secreted and expressed in COS-1/pSV2CNP cells. One can also see from FIG. 6 that peptides showing immunoreactivety with the anti-CNP-22 antiserum occurred at molecular weights of ca. 3–7 kd. This also led to the conclusion that part of Pro CNP was further converted to peptides of lower molecular weights (each having a CNP-22 structure in its C-terminal region) in COS-1 cells.

In summary, the present inventors isolated chromosomal genes and cDNAs coding for the presurcor proteins of porcine CNPs (CNP-22 and CNP-53) and analyzed them to identify the primary amino acid sequences of the porcine CNP precursor proteins. At the same time, they successfully produced by a genetic engineering method all or part of the proteins encoded by that gene or cDNA. The present invention has been accomplished under these circumstances.

The following examples are provided for the purpose of further illustrating the present invention but are in no way to be taken as limiting.

Example 1

Preparation of DNA probe (DC-53)

A. Gene amplification by PCR

The chromosomal gene region coding for the primary amino sequence of CNP-53 was amplified in vitro by the following method. First, two DNA primers (KF 225 and KF 226) that corresponded to the primary amino acid sequence of CNP-53 in its N- and C-terminal regions (see FIG. 1) were synthesized chemically. A restriction enzyme (PstI) recognition site was introduced artificially into the 5' terminal regions of KF 225 and KF 226 so as to facilitate the sub-cloning of the gene after its amplification (in FIG. 1, the artificially converted bases are indicated by small letters of alphabets). Subsequently, using those DNA primers, polymerase chain reaction (PCR) was performed in accordance with the method of Saiki et al. (Saiki, P. K. et al., Science, 239, 487, 1988) by the following procedure. KF 225 and KF 226 each weighing 1.26 μg and a porcine DNA (1 μg) were added to 100 μl of a reaction solution [10 mM Tris-HCl (pH 8.5), 2.5 mM $MgCl_2$, 50 mM KCl, 0.2 mM NPTs, and 0.02% gelatin]. To the solution, 5 units of Thermus aquaticus DNA polymerase (New England BioLabs) was added for performing PCR through 30 cycles, each cycle consisting of successive heating at 90° C. for 1.5 min, at 65° C. for 2 min and at 70° C. for 1.5 min. At cycle 10, 5 more units of the DNA polymerase mentioned above was added to the reaction solution. The genes amplified in this way were recovered by ethanol precipitation.

B. Subcloning and Analysis of DC-53

For obtaining a DNA fragment coding for the primary amino acid sequence of the desired CNP-53, the DNA fragments amplified in A were subcloned into a plasmid vector pUC 118 before the amplified genes were treated with a restriction enzyme PstI. The treated gene fragments were introduced into PUC 118 (Takara Shuzo Co., Ltd.) at PstI site, which was used to transform E. coli strain 12 derived DH1 to prepare a gene library. Subsequently, the gene library was screened using a chemically synthesized mixed DNA probe KF 206 (oligonucleotide mixed DNA probe corresponding to the portion of the primary amino sequence of CNP-53 shown in FIG. 1 that started with leucine (Lcu) at position 16 and ending with asparagine (Asn) at position 21; 32 mixtures of 14 mers) in accordance with the method of Wood (Wood, W. I. et al., Proc. Natl. Acad. Sci. U.S.A., 82, 1585, 1985), whereby a clone DH1/pCNP5 hybridizing with KF 206 was obtained. In a subsequent step, a plasmid (pCNP5) was separated and purified from the clone in the usual manner. The purified plasmid was cleaved with a restriction enzyme PstI. Upon analysis, pCNP5 was found to contain a PstI DNA fragment composed of ca. 150 bp. In order to verify that the PstI DNA fragment was a gene fragment coding for the primary amino acid sequence of the final target CNP-53, said PstI DNA fragment was cloned in M13 phage and the DNA base sequence of interest was determined with SEQUENASE (United States Biochemical Corporation) by the dideoxy method, (Sanger, F. et al., Proc. Natl. Acad. Sci. U.S.A., 74, 5463, 1977). As a result, it was found that the PstI DNA fragment was a gene composed of a total of 147 bp and having a DNA base sequence coding for CNP-53.

C. Preparation of DC-53

A DNA probe (DC-53) to be used in cloning a gene coding for the porcine CNP precursor protein was prepared by a method that consisted of cleaving the aforementioned plasmid pCNP 5 with a restriction enzyme PstI, isolating a 147-bp DNA fragment, and radiolabelling the DNA fragment by nick translation using $(\alpha-^{32}P)$ dCTP.

Example 2

Isolation of Chromosomal Gene Coding for Porcine CNP Precursor Protein

E. coli strain K12 derived LE 392 was infected with a porcine chromosomal gene phage DNA library (product of Clonetech Co.) stored at 4° C. The cells were plated on an LB medium (10 g, bactotryptone; 5 g, yeast extract; 5 g, NaCl; 1.5%, bactoagar; total volume, 1 l) and cultivated overnight at 37° C. The plate was cooled at 4° C. for 30 min and a nitrocellulose filter (product of Shleicher & Schnell Co.) was left to stand on the phage plaque for 5 minutes. Subsequently, the filter was stripped from the plate, dried with air, immersed in an alkaline denaturation solution (0.5 M NaOH and 1.5 M NaCl) for 1 minute, and then immersed in a neutralizing solution (0.5 M Tris-HCl; pH 7.0; 1.5 M NaCl) for 1 minute. Thereafter, the nitrocellulose filter was rinsed with a 3×SSC solution (20×SSC NaCl, 175.3 g; trisodium citrate, 88.2 g; total volume, 1 l ), dried with air and heat-treated under vacuum at 80° C. for 120 min.

Using the thus prepared nitrocellulose filter, plaque hybridization was performed under the following conditions. First, a prehybridization solution [3×SSC; 1×Denhardt's solution (consisting of albumin, polyvinyl pyrrolidone and Ficoll, each weighing 0.2 mg/ml); salmon sperm DNA, 50 μg/ml; 0.1% SDS) was added to the nitrocellulose filter and prehybridization was conducted at 65° C. for 3 hours. Then, using 106 cpm of the DC-53 DNA probe and 1 m of the prehybridization solution for two sheets of the nitrocellulose filter, hybridization was performed overnight at 65° C. Subsequently, the filter was washed three times with a 3×SSC solution containing 0.1% SDS, each washing done at 65° C. for 30 minutes; the washed filter was dried with air and subjected to autoradiography at −80° C. for 24 h. By screening ca. $2 \times 10^6$ clones in this way, five clones hybridizing with the DC-53 DNA probe were obtained. One of those clones was named "CNP6" and subjected to analyses in the subsequent stages.

Example 3

Analysis of λCNP6 Phage and Determination of its Base Sequence

A. analysis of λCNP6 phage DNA

DNA was prepared from λCNP6 phage in the usual manner. Subsequently, the phage DNA was cleaved with restriction enzymes BamHI, HindIII and PstI and the resulting DNA fragments were separated and analyzed by electrophoresis on an agarose gel. The λCNP6 was found to be a phage containing a ca. 14-kbp porcine chromosomal gene. Analysis by Southern boltting using the DC-53 DNA probe showed that each of BamHI DNA fragment of ca. 2 kbp, HindIII DNA fragment of ca. 3 kbp and PstI DNA fragment of ca. 5 kbp hybridized with the DC-53 DNA probe. The total base sequence of the BamHI DNA having the lowest molecular weight (2 kbp) of those three fragments which hybridized with the DC-53 DNA probe was determined by the following method for each of the upper and lower strands.

B. Determining the Base Sequence of BamHI DNA Fragment

In order to determine the base sequence of the upper strand of the BamHI DNA fragment, the latter was first subcloned in a plasmid vector pUC 118 (Takara Shuzo Co., Ltd.) at the BamHI site to prepare pUC CNP6. Then, pUC CNP6 was cleaved with restriction enzymes XbaI and SphI and, using a TAKARA kilosequencing deletion kit (Takara Shuzo Co., Ltd.) deletion plasmids, or plasmids having the left-hand DNA terminus of BamHI DNA deleted in varying lengths as shown in FIG. 2(a), were prepared. Subsequently, the length of deletion was analyzed by electrophoresis on an agarose gel and 9 clones deleted to appropriate lengths were selected. Finally, those clones were infected with a helper phage M13K07 and a single-stranded DNA (upper strand) was recovered. Using a universal primer, with the recovered DNA being used as a template, the DNA base sequence of the upper strand of the BamHI DNA fragment was determined by the dideoxy method with SEQUENASE (United States Biochemical Corporation). As for the regions whose base sequences could not be determined on account of the non-availability of deletion mutant clones of appropriate lengths by the method described above, their DNA base sequences were determined using as a primer the oligonucleotides KF 248, KF 249 and KF 250 [see FIG. 2(c)] that were chemically synthesized on the basis of the already determined base sequences.

As regards the base sequence of the lower strand, the upper strand of a 2-kbp BamHI DNA fragment was subdloned in M13 phage and, with the subclone being used as a template, the base sequence was determined by the dideoxy method using a universal primer and the oligonucleotide primers, KF 239, KF 243, KF 244, KF 245, KF 246, KF 247, KF 252 and KF 254 [see FIG. 2(c)], that were chemically synthesized on the basis of the base sequence of the upper strand which was determined by the aforementioned procedure. The regions whose base sequences were determined using a universal primer are identified by solid arrows in FIG. 2(b) and those whose base sequences were determined using chemically synthesized oligonucleotide primers are identified by dashed arrows in FIG. 2(b).

The base sequence of the upper strand of the BamHI DNA fragment which was determined by the above-described method and the amino acid sequence encoded at the exon sites as predictable from that base sequence are shown in FIG. 3.

Example 4

Expression of Porcine CNP Gene

Using the porcine CNP precursor gene (BamHI DNA fragment) isolated and analyzed in Example 3, the structural gene region of the porcine CNP precursor gene was expressed in animal cells and not only the structure of mRNA transcribed from said structural gene but also the protein translated from said mRNA were analyzed.

A. Preparation of Porcine CNP Structural Gene Expression Vector pSV2CNP

As shown in FIG. 4, a plasmid vector pSV2dhfr (Bethesda Research Laboratories, Inc.) was first cleaved with a restriction enzyme Bgl II. Subsequently, the sites cleaved with Bgl II were rendered to have a blunt end and thereafter treated with a restriction enzyme HindIII to eliminate the CDNA region of a mouse dehydrofolic acid reductase (mouse dhfr) from the pSV2dhfr. In the next place, a plasmid pUC CNPdel (which plasmid was one of the deletion plasmids prepared in Example 3 when the base sequence of the upper strand DNA of the BamHI DNA fragment was determined and it has 166 bp deleted from the 5'-terminus of the BamHI DNA fragment shown in FIG. 3; the host cell transformed with this plasmid was named "Escherichia coli SMB318" and has been deposited with the Fermentation Research Institute, the Agency of Industrial Science and Technology on Jul. 10, 1990 under Accession Number 2997 (FERM BP-2997)] was cleaved with restriction enzymes HindIII and RsaI to obtain a DNA fragment composed of 989 bp. This DNA fragment was ligated with the HindIII-Bgl II DNA fragment of pSV2dhfr which had been prepared by the aforementioned method, whereupon a porcine CNP structural gene expression vector pSV2CNP was prepared.

B. Analysis of mRNA transcribed from pSV2CNP
The structure of mRNA transcribed from the porcine CNP structural gene was analyzed by the following procedure.

First, plasmid pSV2CNP (10 μg) was introduced into monkey kidney derived COS-1 cells ($7.5 \times 10^5$ cells) using Cellphect Transfection Kit (Pharmacia). The transfected cells were cultivated in 8 ml of a DMEM (Dulbeco's Modified Eagle's Medium, GIBCO) containing 10% FCS (fetal calf serum, GIBCO) in the presence of $CO_2$ at 37° C. for 72 h. Thereafter, the supernatant of the culture was separated from the cells. The thus obtained culture supernatant was stored at −70° C. and used in protein analysis as will be described in C below. On the other hand, the cells were used in mRNA analysis as described just below.

Using a guanidine-thiocyanate method, 800 μg of total RNA was extracted from ca. $10^7$ cells of COS-1/pSV2CNP. Then, using an oligo(dT)-cellulose column, ca. 150 μg of poly(A)$^+$ RNA was prepared from 800 μg of total RNA. Subsequently, using 10 μg of poly(A)+RNA, a cDNA library was prepared by the method of Okayama-Berg (Molec. Cell Biol., 2, 161–170, 1982) to obtain ca. $2 \times 10^5$ independent clones. The cDNA library consisting of ca. $4 \times 10^3$ clones was screened in the usual manner using the DC-53 DNA probe prepared in Example 1, whereby clones hybridizing with the DC-53 DNA probe were obtained and named "DHl/pCNP cDNA 1".

In a subsequent step, plasmid (pCNP cDNA 1) was separated and purified from the clones in the usual manner, cleaved with various restriction enzymes and analyzed. As a result, the pCNP cDNA 1 was found to contain ca. 14 kb of CDNA. For final analysis of mRNA, the 1.4-kb cDNA was subdloned in M13 phage and the base sequence of DNA was determined by the dideoxy method using SEQUENASE (United States Biochemical Corporation). FIG. 5 shows the thus determined DNA base sequence of cDNA and the primary amino acid sequence predictable from the DNA base sequence.

C. Analysis of Protein Translated from CNP mRNA

The protein translated from CNP MRNA was analyzed by the following procedure. First, the supernatant (75 ml) of COS-1/pSV2CNP prepared in Example 4-B was dissolved, followed by concentration and salting-out with Sep-pak. Then, the sample was lyophilized and dissolved in 5 ml of 1 M acetic acid solution. Subsequently, the proteins and peptides contained in the solution were fractionated on a Sephadex G-75 column (1.8×137 cm, Pharmacia) in accordance with molecular weight (flow rate: 7.7 ml/h; fraction size: 5 ml). Finally, a portion (40 μl) of each eluted fraction was subjected to a radioimmunoassay (RIA) system using an anti-CNP-22 antiserum [for details of the RIA system, see the commonly assigned patent application on a novel porcine physiologically active peptide (CNP-53)] to determine the quantities of peptide and protein (ir-CNP-22) that was present in each fraction and that showed immunoreactivity with the anti-CNP-22 antibody.

The result is shown in FIG. 6, from which one can see that a protein and peptide showing immunoreactivity with the anti-CNP-22 antiserum occurred in eluted fractions (≠36–4) with molecular weights of ca. 16 kd and in eluted fractions (≠45–66) with molecular weights of 3–10 kd. The results of RIA also showed that the culture supernatant of COS-1/pSV2CNP contained 150 ng, in terms of CNP-22, of a protein and peptide that exhibited immunoreactivity with the anti-CNP-22 antiserum.

In accordance with the present invention, the DNA region of a porcine chromosomal gene that coded for CNP-53 was specifically amplified by PCR to prepare a DNA probe (DC-53). Subsequently, using the DC-53, a chromosomal gene coding for the porcine CNP (CNP-22 and CNP-53) precursor protein was isolated and its structure was identified. As shown in FIG. 3, the BamHI DNA fragment isolated in the present invention was found to contain not only the structural gene region coding for the whole amino acid sequence of the porcine CNP precursor protein (which is encoded in two exons in its structural gene region) but also the promoter region of the porcine CNP gene.

In the next step, the structural gene region of the chromosomal gene was expressed in monkey kidney derived COS-1 cells and the structure of mRNA (cDNA) transcribed from the structural gene as well as the protein translated from the mRNA were analyzed. As a result, the porcine CNP precursor protein was found to be a polypeptide that had the primary amino acid sequence shown in FIG. 5 and that was composed of 126 amino acid residues in total. It was also found that a signal peptide was present in the N-terminal region of the precursor protein (prepro CNP) and that both CNP-22 and CNP-53 in vivo were peptides that were secreted out of cells. It was further found that by expressing the porcine CNP structural gene in animal cells, a peptide and protein showing immunoreactivity with an anti-CNP-22 antibody could be produced.

The genes and cDNAs of porcine CNP precursors were isolated and identified by the present invention. If they are used as DNA probes, the gene or cDNA of CNP derived from the cells of other animals than pig can be isolated and by analysing them, the CNP of non-porcine animals can be identified. As shown in Example 4-C, the gene or cDNA coding for the porcine CNP precursor can be expressed in animal cells and the protein or peptide that is secreted out of cells can be isolated and identified to provide more detailed information about the mechanism behind the biosynthesis of porcine CNPs. Pro CNP which lacks a signal peptide from pre pro CNP has not so far been isolated and identified in vivo, nor have been various peptides that have additional amino acids attached to the N-terminus of CNP-53 [at least 5 lysine (Lys) residues and at least 3 arginine (Arg) residues are present in the primary amino acid sequence of pre pro CNP between positions 24 and 73, with Lys at positions 30, 51, 52, 55 and 65 and Arg at positions 33, 68 and 70, so pro CNP is likely to be cleaved specifically in vivo at the C-terminus of any one of those basic amino acid residues with processing enzymes and, besides CNP-22 and CNP-53 which have so far been identified in vivo, there is high possibility for the occurrence of peptides having additional amino acids attached to the N-terminus of CNP-53] but, in accordance with the present invention, even those peptides can be isolated and identified for the purpose of examining their physiological activities.

It was further found that the gene of porcine CNP precursor protein shown in FIG. 3 contained not only a structural gene region coding for the porcine CNP precursor but also a promoter region capable of expressing the structural gene of interest. In view of the fact that CNP-22 and CNP-53 were isolated from the brain, the promoter will most probably work in the brain in a specific manner. Hence, if a gene coding for a suitable protein is linked downstream of the promoter and if the combination is used to prepare a transgenic mouse, the protein of interest can be expressed specifically in the brain of the transgenic mouse, making it possible to analyze the physiological actions of the protein at the individual level.

The information obtained by the present invention concerning the chromosomal gene, cDNA and primary amino acid sequence of porcine CNP precursor proteins will make great contributions not only to future studies for unravelling the mechanism behind the biosynthesis and physiological actions of CNP in mammals but also to the efforts to establish pharmaceutical applications of peptides assignable to the CNP family.

What is claimed is:

1. A polypeptide having the following amino acid sequence (see SEQ. ID. NO. 20):

```
Met His Leu Ser Gln Leu Leu Ala Cys Ala

Leu Leu Leu Thr Leu Leu Ser Leu Arg Pro

Ser Glu Ala Lys Pro Gly Ala Pro Pro Lys

Val Pro Arg Thr Pro Pro Gly Glu Glu Val

Ala Glu Pro Gln Ala Ala Gly Gly Gly Gln

Lys Lys Gly Asp Lys Thr Pro Gly Gly Gly

Gly Ala Asn Leu Lys Gly Asp Arg Ser Arg

Leu Leu Arg Asp Leu Arg Val Asp Thr Lys

Ser Arg Ala Ala Trp Ala Arg Leu Leu His

Glu His Pro Asn Ala Arg Lys Tyr Lys Gly

Gly Asn Lys Lys Gly Leu Ser Lys Gly Cys

Phe Gly Leu Lys Leu Asp Arg Ile Gly Ser

Met Ser Gly Leu Gly Cys.
+PS
```

2. A polypeptide according to claim 1 which lacks a signal peptide from said amino acid sequence at the N-terminus.

3. A DNA coding for a polypeptide (CNP-22) having the following amino acid sequence (see SEQ. ID. NO. 21):

```
Gly Leu Ser Lys Gly Cys Phe Gly Leu Lys Leu

Asp Arg Ile Gly Ser Met Ser Gly Leu Gly Cys.
```

4. A DNA according to claim 3 which comprises the following base sequence (see SEQ. ID. NO. 14):

```
GGT TTG TCC AAG GGC TGC TTC GGC CTC AAA CTG

GAC CGG ATC GGC TCC ATG AGC GGC CTG GGA TGT.
```

5. A DNA coding for a polypeptide (CNP-53) having the following amino acid sequence (see SEQ. ID. NO. 22):

```
Asp Leu Arg Val Asp Thr Lys Ser Arg Ala Ala

Trp Ala Arg Leu Leu His Glu His Pro Asn Ala

Arg Lys Tyr Lys Gly Gly Asn Lys Lys Gly Leu

Ser Lys Gly Cys Phe Gly Leu Lys Leu Asp Arg

Ile Gly Ser Met Ser Gly Leu Gly Cys.
```

6. A DNA according to claim 5 which comprises the following base sequence (see SEQ. ID. NO. 15):

```
GAC CTG CGC GTG GAC ACC AAG TCT CGG GCG GCG

TGG GCC CGC CTT CTG CAC GAG CAC CCC AAC GCG
```

```
CGC AAA TAC AAA GGA GGC AAC AAG AAG GGT TTG

TCC AAG GGC TGC TTC GGC CTC AAA CTG GAC CGG

ATC GGC TCC ATG AGC GGC CTG GGA TGT.
```

7. A DNA coding for a polypeptide having the following amino acid sequence (see SEQ. ID. NO. 20):

```
Met His Leu Ser Gln Leu Leu Ala Cys Ala

Leu Leu Leu Thr Leu Leu Ser Leu Arg Pro

Ser Glu Ala Lys Pro Gly Ala Pro Pro Lys

Val Pro Arg Thr Pro Pro Gly Glu Glu Val

Ala Glu Pro Gln Ala Ala Gly Gly Gly Gln

Lys Lys Gly Asp Lys Thr Pro Gly Gly Gly

Gly Ala Asn Leu Lys Gly Asp Arg Ser Arg

Leu Leu Arg Asp Leu Arg Val Asp Thr Lys

Ser Arg Ala Ala Trp Ala Arg Leu Leu His

Glu His Pro Asn Ala Arg Lys Tyr Lys Gly

Gly Asn Lys Lys Gly Leu Ser Lys Gly Cys

Phe Gly Leu Lys Leu Asp Arg Ile Gly Ser

Met Ser Gly Leu Gly Cys.
```

8. A DNA according to claim 7 which comprises the following base sequence (see SEQ. ID. NO. 16):

```
ATG CAC CTC TCC CAG CTG CTG GCC TGC GCT

CTG CTG CTC ACG CTC CTC TCG CTC CGG CCC

TCC GAA GCC AAG CCC GGA GCG CCG CCG AAG

GTC CCT CGA ACT CCG CCA GGG GAG GAG GTG

GCC GAG CCC CAG GCT GCG GGC GGC GGT CAG

AAG AAG GGC GAC AAG ACT CCT GGG GGC GGT

GGC GCC AAC CTC AAG GGC GAC CGG TCT CGA

CTG CTG CGG GAC CTG CGC GTG GAC ACC AAG

TCT CGG GCG GCG TGG GCC CGC CTT CTG CAC

GAG CAC CCC AAC GCG CGC AAA TAC AAA GGA

GGC AAC AAG AAG GGT TTG TCC AAG GGC TGC

TTC GGC CTC AAA CTG GAC CGG ATC GGC TCC

ATG AGC GGC CTG GGA TGT.
```

9. A DNA coding for a portion of a polypeptide having the following amino acid sequence (see SEQ. ID. NO. 20), said portion being one that is left after a signal peptide is deleted from at the N-terminus:

```
Met His Leu Ser Gln Leu Leu Ala Cys Ala

Leu Leu Leu Thr Leu Leu Ser Leu Arg Pro

Ser Glu Ala Lys Pro Gly Ala Pro Pro Lys

Val Pro Arg Thr Pro Pro Gly Glu Glu Val

Ala Glu Pro Gln Ala Ala Gly Gly Gly Gln

Lys Lys Gly Asp Lys Thr Pro Gly Gly Gly

Gly Ala Asn Leu Lys Gly Asp Arg Ser Arg

Leu Leu Arg Asp Leu Arg Val Asp Thr Lys

Ser Arg Ala Ala Trp Ala Arg Leu Leu His

Glu His Pro Asn Ala Arg Lys Tyr Lys Gly

Gly Asn Lys Lys Gly Leu Ser Lys Gly Cys

Phe Gly Leu Lys Leu Asp Arg Ile Gly Ser

Met Ser Gly Leu Gly Cys.
```

10. A DNA comprising the following base sequence (see SEQ. ID. NO. 2):

```
            GCACCCAGCCGGCGCCGCGCAGCACT
GGGACTCGCGCCCGCACCGCAGCCCGGCCAGTCTGCTCC
GCGCTCGCTTGCCAGTCTGCCCGCCGGCCCCGTGCACCT
CTCTGCCGCCGATCTGCGCCCCTCCACCCCACAGGCACC
ATG CAC CTC TCC CAG CTG CTG GCC TGC GCT
CTG CTG CTC ACG CTC CTC TCG CTC CGG CCC
TCC GAA GCC AAG CCC GGA GCG CCG CCG AAG
GTC CCT CGA ACT CCG CCA GGG GAG GAG GTG
GCC GAG CCC CAG GCT GCG GGC GGC GGT CAG
AAG AAG GGC GAC AAG ACT CCT GGG GGC GGT
GGC GCC AAC CTC AAG GGC GAC CGG TCT CGA
CTG CTC CGG GAC CTG CGC GTG GAC ACC AAG
TCT CGG GCG GCG TGG GCC CGC CTT CTG CAC
GAG CAC CCC AAC GCG CGC AAA TAC AAA GGA
GGC AAC AAG AAG GGT TTG TCC AAG GGC TGC
TTC GGC CTC AAA CTG GAC CGG ATC GGC TCC
ATG AGC GGC CTG GGA TGT TAG TGC GGCGACC
CCTGGCGGCGGTGAG.
```

11. A DNA comprising the base sequence shown in FIG. 3 (see SEQ. ID. NO. 1).

12. A process for producing a polypeptide (CNP-22) having the following amino acid sequence:

```
Gly Leu Ser Lys Gly Cys Phe Gly Leu Lys Leu
Asp Arg Ile Gly Ser Met Ser Gly Leu Gly Cys
``` which comprises inserting into a plasmid vector a DNA sequence coding for a porcine CNP precursor to form an expression vector, transforming a mammalian host cell with the expression vector, culturing the transformed cells, and recovering and isolating CNP-22 from the culture.

13. The process of claim 12, wherein the plasmid vector is pUC CNPdel.

14. The process of claim 12, wherein the expression vector is pSV2CNP.

15. The process of claim 12, wherein the host cell is a mammalian cell.

* * * * *

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
        (A) LENGTH: 1894 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:1:

```
GGATCCCTCC GGGGTGGGAA GAGGGTGGGG GCAGAGGGGG AGCCCCCGCG GCCCCCTCCC      60

GGCCTTCGGC GCGCGTGCCA TTGGCCCGGG CGGCCTTGTG GGCGGGAGGA TGACATCAGC     120

GGCAGGTTGG ATTATAAAGG CGCGAGCGGA GCCACGGGCT CAGAGCGCAC CCAGCCGGCG     180

CCGCGCAGCA CTGGGACTCG CGCCCGCACC GCAGCCCGGC CAGTCTGCTC CGCGCTCGCT     240

TGCCAGTCTG CCCGCCGGCC CCGTGCACCT CTCTGCCGCC GATCTGCGCC CCTCCACCCC     300

ACAGGCACCA TGCACCTCTC CCAGCTGCTG GCCTGCGCTC TGCTGCTCAC GCTCCTCTCG     360

CTCCGGCCCT CCGAAGCCAA GCCCGGAGCG CCGCCGAAGG TGGGTGCTGT CGCAGGGACG     420

TCGGAACTGT GAGGGGCCGT GGCACGGCTG GGGGGGTCTA GGAGGGTGCG GCGCGCCAGA     480

AGCAGCAGAG GGGCCAGGAA GGCGGCTCTC TCCCCAGATG TGCGCCGGTA AGAGCTGGGG     540

CGCCTTCGAA GCCTGGGGAG AACGTCTGCA AACGCGCAGC CGCTGCCCCA GCGTGGTCAG     600

CCGGGCAGGG GGCAGAGGAG AAGAGGGCGA GGGACTCCCT GAGGAAGGGG ACAGCGGCGG     660

CCGCGTGGCA GGTGGATGCA GGGCCCAACT ATCCTGCACC TGTGGGGGAG CGCTCAGGGC     720

TTGAAAGGGA CAAACCGCGC CGGCGGGCGT GTCGCCCTGG AGCATCAGCG GCCCCACAAA     780

GTCCCCCGCC CTGCCGTCGT GCGTCCCTTC ACTTACCTGT TCTTTCCCCC TCGGACAGGT     840

CCCTCGAACT CCGCCAGGGG AGGAGGTGGC CGAGCCCCAG GCTGCGGGCG GCGGTCAGAA     900

GAAGGGCGAC AAGACTCCTG GGGCGGTGG CGCCAACCTC AAGGGCGACC GGTCTCGACT     960

GCTCCGGGAC CTGCGCGTGG ACACCAAGTC TCGGGCGGCG TGGGCCCGCC TTCTGCACGA    1020

GCACCCCAAC GCGCGCAAAT ACAAAGGAGG CAACAAGAAG GGTTTGTCCA AGGGCTGCTT    1080

CGGCCTCAAA CTGGACCGGA TCGGCTCCAT GAGCGGCCTG GGATGTTAGT GCGGCGACCC    1140

CTGGCGGCGG TGAGTACCAC CCAACCCTGG CCTCCGGGCG CTCTTGGCAC ACCCAGCTCC    1200

CCCGAGAAGG CCCCCAGAAC CAAGCCTGAA CCCCGTGCCG CAAGCCGGTC TCCCTCTGAT    1260

CCCCAGACTT TGGGACCATT CCGCCTCCCA GCCGACCTTT GGAGGGGAGC CAACCGACTC    1320

CAGCACAAGA CTGAGGGCGT GTGCCAGACA TTTGTCCCAA GACCGTTTAT CATTCCATTT    1380

CACAGATGGG GGAAATTGAG GGATAAAGTG GCCAGGTAAT TTTGGCAAGG TCAGAAGCGG    1440

CTCAGCATGG ATGAACGCAC CTGGCTGCCT CTGGGGAAAC AGGCAGCTTG GTGGAGTCCT    1500

GCCCATCCCA GGAACATAAG GCAGCCAGCA GCACTGGCCC CAGTTTGCCA GTTGGGGGGT    1560

CTTGAAGAGT GATCCTGGGC TGATGGGAGC AGAGGAGGAA GGGCAGACCC ACAGGTCAAG    1620
```

-continued

```
GGTAAGTTTA TCTGCCAGCC CCTGCATCTT GGTGCTGGGC AGTAAGTAGC CCAGTGGTCA       1680

GGACAGCTCC CTGGGTCTGT TGTCCCTGAA ATGGGACCGA CGCGGATCAA GATCCGTGCC       1740

CTCACGGTCG AGAGAATAGC CCTCTGTTGG CATCACGGAG GTGCATTCTG CCCCAGAACA       1800

TTCTGGCTCT TGTCCCTTCT CTAAACCATG GCTGTGGGCA AACTGGTCTG TCCAGGGTCC       1860

TGACGCCTCT GCAGCCTGTG CGACTTCAGG ATCC                                  1894
```

(2) INFORMATION FOR SEQ ID NO:2:

(i) SEQUENCE CHARACTERISTICS:
        (A) LENGTH: 549 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

```
GCACCCAGCC GGCGCCGCGC AGCACTGGGA CTCGCGCCCG CACCGCAGCC CGGCCAGTCT         60

GCTCCGCGCT CGCTTGCCAG TCTGCCCGCC GGCCCCGTGC ACCTCTCTGC CGCCGATCTG        120

CGCCCCTCCA CCCCACAGGC ACCATGCACC TCTCCCAGCT GCTGGCCTGC GCTCTGCTGC        180

TCACGCTCCT CTCGCTCCGG CCCTCCGAAG CCAAGCCCGG AGCGCCGCCG AAGGTCCCTC        240

GAACTCCGCC AGGGGAGGAG GTGGCCGAGC CCCAGGCTGC GGGCGGCGGT CAGAAGAAGG        300

GCGACAAGAC TCCTGGGGGC GGTGGCGCCA ACCTCAAGGG CGACCGGTCT CGACTGCTCC        360

GGGACCTGCG CGTGGACACC AAGTCTCGGG CGGCGTGGGC CCGCCTTCTG CACGAGCACC        420

CCAACGCGCG CAAATACAAA GGAGGCAACA AGAAGGGTTT GTCCAAGGGC TGCTTCGGCC        480

TCAAACTGGA CCGGATCGGC TCCATGAGCG GCCTGGGATG TTAGTGCGGC GACCCCTGGC        540

GGCGGTGAG                                                               549
```

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

```
CTTGGACAAA CCCTTCTTGT TG                                                 22
```

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:4:

```
GGGGCTGGCA GATAAAC                                                       17
```

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: double (D) TOPOLOGY: linear (ii) MOLECULE TYPE: DNA (genomic)

(xi) SEQUENCE DESCRIPTION: SEQ ID NO:5:

AGCCGCTTCT GACCTTG                                                  17

(2) INFORMATION FOR SEQ ID NO:6:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:6:

GTGAAGGGAC GCACGAC                                                  17

(2) INFORMATION FOR SEQ ID NO:7:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:7:

TACCGGCGCA CATCTGG                                                  17

(2) INFORMATION FOR SEQ ID NO:8:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:8:

GTCCCAGTGC TGCGCGG                                                  17

(2) INFORMATION FOR SEQ ID NO:9:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:9:

CCGCGCAGCA CTGGGAC                                                  17

(2) INFORMATION FOR SEQ ID NO:10:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:10:

```
CCCAGATGTG CGCCGGT                                                    17

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:11:

CAAGGTCAGA AGCGGCT                                                    17

(2) INFORMATION FOR SEQ ID NO:12:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:12:

AGACCGGCTT GCGGCAC                                                    17

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:13:

GCTTCGGAGG GCCGGAG                                                    17

(2) INFORMATION FOR SEQ ID NO:14:

(i) SEQUENCE CHARACTERISTICS:
        (A) LENGTH: 66 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:14:

GGTTTGTCCA AGGGCTGCTT CGGCCTCAAA CTGGACCGGA TCGGCTCCAT GAGCGGCCTG      60

GGATGT                                                                66

(2) INFORMATION FOR SEQ ID NO:15:

(i) SEQUENCE CHARACTERISTICS:
        (A) LENGTH: 159 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:15:

GACCTGCGCG TGGACACCAA GTCTCGGGCG GCGTGGGCCC GCCTTCTGCA CGAGCACCCC      60
```

-continued

```
AACGCGCGCA AATACAAAGG AGGCAACAAG AAGGGTTTGT CCAAGGGCTG CTTCGGCCTC        120

AAACTGGACC GGATCGGCTC CATGAGCGGC CTGGGATGT                               159
```

(2) INFORMATION FOR SEQ ID NO:16:

(i) SEQUENCE CHARACTERISTICS:
        (A) LENGTH: 378 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:16:

```
ATGCACCTCT CCCAGCTGCT GGCCTGCGCT CTGCTGCTCA CGCTCCTCTC GCTCCGGCCC         60

TCCGAAGCCA AGCCCGGAGC GCCGCCGAAG GTCCCTCGAA CTCCGCCAGG GGAGGAGGTG        120

GCCGAGCCCC AGGCTGCGGG CGGCGGTCAG AAGAAGGGCG ACAAGACTCC TGGGGGCGGT        180

GGCGCCAACC TCAAGGGCGA CCGGTCTCGA CTGCTCCGGG ACCTGCGCGT GGACACCAAG        240

TCTCGGGCGG CGTGGGCCCG CCTTCTGCAC GAGCACCCCA ACGCGCGCAA ATACAAGGA         300

GGCAACAAGA AGGGTTTGTC CAAGGGCTGC TTCGGCCTCA AACTGGACCG GATCGGCTCC        360

ATGAGCGGCC TGGGATGT                                                     378
```

(2) INFORMATION FOR SEQ ID NO:17:

(i) SEQUENCE CHARACTERISTICS:
        (A) LENGTH: 38 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:17:

```
GACCTGCAGG TGGACACCAA GTCCCGGGCT GCCTGGGC                                 38
```

(2) INFORMATION FOR SEQ ID NO:18:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:18:

```
GTRCTYGTRG GNTT                                                          14
```

(2) INFORMATION FOR SEQ ID NO:19:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:19:

```
TTCGACCTGG CCTAACCGAG GTACAGACCG GACGTCACG                                39
```

(2) INFORMATION FOR SEQ ID NO:20:

(i) SEQUENCE CHARACTERISTICS:

(A) LENGTH: 126 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:20:

Met His Leu Ser Gln Leu Leu Ala Cys Ala Leu Leu Thr Leu Leu
1               5                  10                  15

Ser Leu Arg Pro Ser Glu Ala Lys Pro Gly Ala Pro Lys Val Pro
                20                  25                  30

Arg Thr Pro Pro Gly Glu Glu Val Ala Glu Pro Gln Ala Ala Gly Gly
            35                  40                  45

Gly Gln Lys Lys Gly Asp Lys Thr Pro Gly Gly Gly Ala Asn Leu
    50                  55                  60

Lys Gly Asp Arg Ser Arg Leu Leu Arg Asp Leu Arg Val Asp Thr Lys
65                  70                  75                  80

Ser Arg Ala Ala Trp Ala Arg Leu Leu His Glu His Pro Asn Ala Arg
                85                  90                  95

Lys Tyr Lys Gly Gly Asn Lys Lys Gly Leu Ser Lys Gly Cys Phe Gly
                100                 105                 110

Leu Lys Leu Asp Arg Ile Gly Ser Met Ser Gly Leu Gly Cys
            115                 120                 125

(2) INFORMATION FOR SEQ ID NO:21:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

Gly Leu Ser Lys Gly Cys Phe Gly Leu Lys Leu Asp Arg Ile Gly Ser
1               5                   10                  15

Met Ser Gly Leu Gly Cys
            20

(2) INFORMATION FOR SEQ ID NO:22:

(i) SEQUENCE CHARACTERISTICS:
        (A) LENGTH: 53 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:22:

Asp Leu Arg Val Asp Thr Lys Ser Arg Ala Ala Trp Ala Arg Leu Leu
1               5                   10                  15

His Glu His Pro Asn Ala Arg Lys Tyr Lys Gly Gly Asn Lys Lys Gly

```
                    20                  25                  30
Leu Ser Lys Gly Cys Phe Gly Leu Lys Leu Asp Arg Ile Gly Ser Met
            35                  40                  45

Ser Gly Leu Gly Cys
        50
```